United States Patent [19]

Shalati et al.

[11] Patent Number: 4,761,289

[45] Date of Patent: Aug. 2, 1988

[54] SUSTAINED RELEASE IMPLANT AND METHOD FOR PREPARING SAME

[75] Inventors: Mohamad D. Shalati, Richton Park, Ill.; Ravi Viswanathan, Miami, Fla.

[73] Assignee: International Minerals & Chemical Corp., Terre Haute, Ind.

[21] Appl. No.: 917,771

[22] Filed: Oct. 10, 1986

[51] Int. Cl.$^4$ .................. A61K 9/00; A61K 15/00; A61K 21/00; A61K 9/22

[52] U.S. Cl. .................. 424/468; 424/475; 427/3

[58] Field of Search .............. 424/468, 475; 427/3

[56] References Cited

U.S. PATENT DOCUMENTS

| | | | |
|---|---|---|---|
| 3,923,939 | 12/1975 | Baker et al. | 264/49 |
| 4,052,505 | 10/1977 | Higuchi et al. | 424/14 |
| 4,164,560 | 8/1979 | Folkman et al. | 424/22 |
| 4,326,525 | 4/1982 | Swanson et al. | 128/260 |
| 4,563,489 | 1/1986 | Urist | 424/78 X |
| 4,610,870 | 9/1986 | Jain et al. | 424/468 X |

OTHER PUBLICATIONS

W. D. Rhine, et al., *J. of Pharmaceutical Sciences*, vol. 69, No. 3, pp. 265–270 (Mar. 1980).

*Primary Examiner*—Michael R. Lusignan
*Attorney, Agent, or Firm*—Thomas L. Farquer; Wendell R. Guffey; George R. Repper

[57] ABSTRACT

A mixture comprising a dispersion of a water-diffusible solid in a solution of a non-aqueous solvent and a substantially water-insoluble polymer is formed. The non-aqueous solvent is removed from the mixture to substantially dry the mixture, and the substantially dry mixture is comminuted to form particles. A plurality of the particles are formed under pressure to produce a pellet suitable for use as a sustained release implant device.

16 Claims, No Drawings

SUSTAINED RELEASE IMPLANT AND METHOD FOR PREPARING SAME

BACKGROUND OF THE INVENTION

1. Field of the Invention

The present invention relates to a sustained release pellet suitable for use as an implant in a living being.

2. Description of the Background Art

In many therapeutic, medical and veterinary programs, it is often desirable and/or necessary to provide for the slow release of a beneficial agent to a living being at a controlled rate over a prolonged period of time.

There have been various approaches in attempting to provide a sustained release device which could release a beneficial agent, such as a drug or hormone, at a controlled rate. One method used is to mix the agent with a carrier material that is gradually broken down by body fluids, the agent being released as the carrier disintegrates. Waxes, oils, fats and soluble polymers are some materials that have been used as the carriers in these sytems.

Methods for producing implants wherein a protein is the beneficial agent (active ingredient) and a polymer is the carrier or matrix material, are known in the art. These methods involve either the casting of a dispersion of a protein in a polymer solution followed by slow removal of solvent from the solution at low temperature (e.g., overnight at −60° C.), or by compression molding of a dry mixture of a protein and polymer particles. The former method produces implants with low density (e.g., 0.75 g/cc) and poor mechanical properties, while the latter method requires high polymer loading with concomitant low protein loading.

There remains a need in the art for a process capable of yielding implants with high protein loading good mechanical properties, and which is capable of being carried out at room temperatures.

SUMMARY OF THE INVENTION

In accordance with the present invention, a method for preparing a pellet containing a water-insoluble polymer and a water-diffusible solid includes the steps of forming a mixture comprising a dispersion of a water-diffusible solid in a solution of a non-aqueous solvent and a water-insoluble polymer. The non-aqueous solvent is removed from the mixture to substantially dry the mixture. The substantially dry mixture then is comminuted to form substantially dry particles and a plurality of the particles are formed under pressure into a pellet.

DESCRIPTION OF THE PREFERRED EMBODIMENTS

A pellet containing a water-insoluble polymer and a water-diffusible solid according to the present invention is administered to a living being, i.e., human or animal, by implantation of the pellet into body tissues, insertion of the device into a body cavity, or oral ingestion by the living being.

The polymer material, with which a diffusible solid is dispersed, becomes a matrix through which the diffusible solid, which is a beneficial agent, must diffuse before entering the fluid medium. Diffusion of the beneficial agent occurs as body fluids gradually penetrate the pellet. The polymer is substantially insoluble in and impermeable to the fluid medium as well as substantially impermeable to the diffusible solid.

The diffusible solid to be used in a pellet according to the present invention may be any agent which produces a beneficial effect in the body of a living being. Beneficial effect is defined as a physiologically or pharmacologically useful effect in the body of a living being either at a site in close proximity to the point of release of the agent, or at a site removed from the release point. Some examples of beneficial agents include hormones, hypnotics, sedatives, antibiotics, tranquilizers, anti-convulsants, muscle relaxants, anti-bloat agents, antipyretics, anti-inflammatories, analgesics, local anethetics, muscle contractants, steroids, anthelmintics, anti-microbials, diuretics, neoplastics, hypoglycemics, amino acids, opthalmic agents, nutritional supplements and vitamins.

According to one embodiment, a biologically active protein, such as a hormone, is utilized as the beneficial, water-diffusible solid agent. In a particularly preferred embodiment, the beneficial agent is an animal growth hormone, such as bovine, porcine or ovine growth hormone.

The polymers used in the matrix with the beneficial agent are bio-compatible with body tissues and body fluids of the living being and substantially insoluble in these body fluids. Body fluids include water and aqueous-based fluid, such as tissue juices, tear fluids, and the like. The term matrix denotes a carrier polymeric phase comprising a polymer that is bio-compatible and sufficiently resistant to chemical and/or physical attack by the environment of use such that the matrices remain substantially intact throughout the prolonged period of time the beneficial agent is released from the pellet. Polymeric matrices useful according to the present invention are bio-compatible in the environment of use and substantially insoluble in and substantially impermeable to the passage of the beneficial agent with which the polymer is mixed. Typical polymeric materials for forming matrices include the naturally occurring and synthetic commercially available polymers such as partially and completely hydrolyzed alkylene-vinyl acetate copolymers; including hydroxylated and unhydroxylated ethylene-vinyl acetate copolymers, polycaprolactone, semi-permeable polyglycolic or polylactic acid and derivatives thereof and derivatives of polystyrene such as poly(sodium styrenesulfonate) and poly(-vinylbenzyltrimethylammonium chloride), acyl-substituted cellulose acetates and alkyl derivatives thereof; unplasticized cellulose acetate, bio-compatible cellulose nitrate, cellulose diacetate, cellulose triacetate, agar acetate, amylose triacetate, beta-glucan acetate, beta-glucan triacetate, cellulose acetate, acetaldehyde dimethyl acetate, cellulose acetate ethyl carbamate, cellulose acetate phthalate, cellulose acetate methyl carbamate, cellulose acetate succinate, cellulose acetate dimethaminoacetate, cellulose acetate ethyl carbonate, cellulose acetate chloroacetate, cellulose acetate ethyl oxatate, cellulose acetate methyl sulfonate, cellulose acetate butyl sulfonate, cellulose acetate propionate, cellulose acetate butyl sulfonate, cellulose acetate propionate, cellulose acetate p-toluene sulfonate, triacetate of locust gum bean, cellulose acetate with acetylated hydroxy-ethyl cellulose, plasticized or unplasticized polyvinyl chloride, homo-and copolymers of polyvinyl acetate, polymers of acrylic acid and methacrylic acid, polyvinyl alkyl ethers, polyvinyl fluoride, polycarbonates, polymeric epoxides, copolymers of an alkylene oxide and alkyl glycidyl ether, polyurethanes, silicone; polyamide; polysulphones, styrene acrylonitrate copolymers; cross-linked poly(ethylene oxide), poly(alkylenes); poly(vinyl) imidazole), poly(esters); and chlorosulphonated polyolefins. These polymeric materials are listed as mere typical examples, and are not to be construed in a limiting sense.

According to one embodiment, a substantially water-insoluble polymer is selected from the group consisting of ethylene-vinyl acetate copolymer, polycaprolactone or polylactic acid.

To prepare the matrix of polymeric material and diffusible solid, the diffusible solid (beneficial agent) is dispersed in a solution of the polymeric material and a non-aqueous solvent. The solvents used in the preparation of pellets according to the invention will depend upon the polymeric material chosen as well as the beneficial agent employed. According to this embodiment, the polymeric material is soluble in the solvent and the beneficial agent is insoluble in the solvent. Methylene dichloride has been found to be a suitable solvent for forming a solution of ethylene/vinyl acetate copolymer, polycaprolactone or polylactic acid, and therein dispersing a protein such as lysozyme or growth hormone as the water-diffusible solid.

The solvent is removed from the dispersion of the water-diffusible solid in the polymer solution by, for example, evaporation under vacuum at room temperature (e.g., for 30 minutes).

The substantially dry mixture from which the solvent has been removed by vacuum evaporation then is comminuted (ground) in, for example, a blender or grinder for approximately 2 minutes to yield fine particles. The resulting particles comprise water-diffusible solid coated with water-insoluble polymer.

A plurality of the particles are formed under pressure to produce a pellet. This can be accomplished by pressing or tableting the particles in a conventional tableting machine to give high density-high loading implants. Any residual amounts of solvent can be removed under vacuum.

A pellet according to the present invention can be formed from a mixture of about 25 to 70 parts by weight of the beneficial agent and from about 75 to 25 parts by weight of polymer. Advantageously the mixture will contain about 40 to 60 parts by weight beneficial agent and from about 60 to 40 parts by weight polymer.

The process of the present invention can be carried out at room temperature to yield a substantially homogeneous implant with high loading and good mechanical properties for subsequent operations such as membrane coating, wax coating, and the like, as is practiced in the implant art.

The invention is further illustrated by the following examples, which are not intended to be limiting.

EXAMPLE I

Lysozyme/Ethylene-Vinyl Acetate Copolymer (EVA) Implant 3.0 g of 250 um Lysozyme was mixed with 5.16 g of 10.3% EVA/$CH_2Cl_2$ solution in a vial. After thorough mixing, the methylene dichloride ($CH_2Cl_2$) was evaporated. The solid mixture was ground in a Janke-Kunkle grinder for approximately 2 minutes. Tablets were made on the Stokes tableting machine. These were used for further studies including dissolution rate, polymer coating, and the like.

EXAMPLE 2

Lysozyme/Polycaprolactone (PCL)

Lyophilized lysozyme was sieved with an ultrasonic sifter to give particles of size $-60 +140$ mesh. One gram of the lysozyme was dispersed in 10 ml of methylene dichloride ($CH_2Cl_2$) containing 0.111 g of polycaprolactone (mol wt.: 31,000 daltons). The slurry was kept in a vortex stirrer for 2 minutes and in an ultrasonic water bath for 16 minutes. The slurry was then transferred to a 100-ml round bottom flask with 20 ml of $CH_2Cl_2$. The $CH_2Cl_2$ was evaporated in a rotary evaporator at room temperature and about 125 mm of pressure. The lysozyme, coated with the polymer, was further dried at room temperature and about 25·mm of pressure. One hundred mg of this solid was placed in the Stokes machine and pellets were made from a setting of 8.2 mm (lengths) and 4 mm (diameter). However, the final pellets were 9 mm (l) and 4 mm (d). The pellets were firm and were used for further studies.

EXAMPLE 3

Bovine Growth Hormone (bGH)/Polylactic Acid (PLA) Implants

Bovine growth hormone (bGH), 800 mg, was suspended in the methylene dichloride ($CH_2Cl_2$) solution (about 1.7 g) containing 141 mg of polylactic acid (mol wt. of (15,600). Evaporation of solvent gave bGH coated with PLA which was dried under vacuum (about 125 mm) at room temperature. Tablets were then made from 106 mg samples using the Stokes machine. The length of the cylinder was 7.2-7.5 mm and the diameter was 4.0 mm. These were coated with PLA and PCL and studied for release profile.

EXAMPLE 4

Bovine Growth Hormone (bGH)/Polycaprolactone (PCL) Implants

In an experiment similar to Example 3, 800 mg of bGH was dispersed in methylene dichloride ($CH_2Cl_2$) solution (about 1.7 g) containing 141 mg of PCL. Evaporation of the solvent gave bGH coated with PCL. Tablets were made as described above and used for further studies.

What is claimed is:

1. A method for preparing a pellet containing effective amount of a substantially water-insoluble polymer and a growth hormone, the method comprising:
    (a) forming a mixture comprising a dispersion of a growth hormone in a solution of a non-aqueous solvent and a substantially water-insoluble polymer:
    (b) removing the non-aqueous solvent from the mixture to substantially dry the mixture;
    (c) comminuting the substantially dry mixture to form particles; and
    (d) forming a plurality of the particles under pressure to produce a pellet.

2. The method of claim 1 wherein the water-insoluble polymers is selected from the group consisting of partially and completely hydrolyzed alkylene-vinyl acetate copolymers; including hydroxylated and unhydroxylated ethylene-vinyl acetate copolymers, polycaprolactone, semi-permeable polyglycolic or polylactic acid and derivatives thereof and derivatives of polystyrene such as poly(sodium styrenesulfonate) and poly(- vinylbenzyltrimethylammonium chloride), acyl-substituted cellulose acetates and alkyl derivatives thereof; unplasticized cellulose acetate, bio-compatible cellulose nitrate, cellulose diacetate, cellulose triacetate, agar acetate, amylose triacetate, beta glucan acetate, beta glucan triacetate, cellulose acetate, acetaldehyde dimethyl acetate, cellulose acetate ethyl carbamate, cellulose acetate phthalate, cellulose acetate methyl carbamate, cellulose acetate succinate, cellulose acetate dimethaminoacetate, cellulose acetate ethyl carbonate, cellulose acetate chloroacetate, cellulose acetate ethyl oxatate, cellulose acetate methyl sulfonate, cellulose acetate butyl sulfonate, cellulose acetate propionate, cellulose acetate butyl sulfonate, cellulose acetate propionate, cellulose acetate p-toluene sulfonate, triacetate of locust gum bean, cellulose acetate with acetylated hydroxy-ethyl cellulose, plasticized or unplasticized polyvinyl chloride, homo-and copolymers of polyvinyl acetate, polymers of acrylic acid and methacrylic acid, polyvinyl alkyl ethers, polyvinyl fluoride, polycarbonates, polymeric epoxides, copolymers of an alkylene oxide and alkyl glycidyl ether, polyurethanes, silicone; polyamide; polysulphones, styrene acrylonitrate copolymers; cross-linked poly(ethylene oxide), poly(alkylenes); poly(vinyl) imidazole), poly(esters); and chlorosulphonated polyolefins.

3. The method of claim 1 wherein the hormone comprises from about 25% to about 75% by weight of said pellet.

4. The method of claim 3 wherein said water-insoluble polymer is ethylene-vinyl acetate copolymer, polycaprolactone or polylactic acid.

5. The method of claim 4 wherein said non-aqueous solvent is methylene dichloride.

6. The method of claim 1 wherein said hormone is bovine growth hormone, porcine growth hormone or ovine growth hormone.

7. The method of claim 3 wherein said growth hormone is bovine growth hormone, porcine growth hormone or ovine growth hormone.

8. The method of claim 2 wherein said hormone is bovine growth hormone, porcine growth hormone or ovine growth hormone.

9. The method of claim 5 wherein said growth hormone is bovine growth hormone, porcine growth hormone or ovine growth hormone.

10. The method of claim 9 further including the step of removing residual non-aqueous solvent from the pellet after forming the pellet.

11. A pellet produced according to the method of claim 1.

12. A method for preparing a pellet containing effective amounts of a substantially water-insoluble polymer and a growth hormone, the method comprising:
 (a) forming a mixture by dispersing a growth hormone selected from the group consisting of bovine, porcine, or ovine growth hormone in a solution of a non-aqueous solvent and a ethylene-vinyl acetate copolymer;
 (b) removing the non-aqueous solvent from the mixture to substantially dry the mixture;
 (c) comminuting the substantially dry mixture to form particles; and
 (d) compression molding a plurality of the particles to form a pellet 13. The method of claim 12 wherein the solvent is methylene dichloride.

14. The method of claim 12 wherein the growth hormone comprises form about 25% to about 75% by weight of said pellet.

15. The method of claim 12 further comprising the step of removing residual solvent from the pellet.

16. A pellet produced according to the method of claim 12.

* * * * *